United States Patent [19]
Faani et al.

[11] 3,932,042
[45] Jan. 13, 1976

[54] CONTAINER INSPECTION APPARATUS AND METHOD OF INSPECTION

[75] Inventors: Siamac Faani; Ralph M. Chambers, Jr., both of Ferguson, Mo.

[73] Assignee: Barry-Wehmiller Company, St. Louis, Mo.

[22] Filed: May 20, 1974

[21] Appl. No.: 471,453

[52] U.S. Cl............ 356/240; 209/111.7; 250/223 B; 356/163
[51] Int. Cl.²................. G01N 21/24; B07C 5/342
[58] Field of Search......... 356/240, 163; 250/223 B; 209/111.7

[56] References Cited
UNITED STATES PATENTS

| | | | |
|---|---|---|---|
| 3,355,980 | 12/1967 | Mathias | 250/223 B X |
| 3,356,853 | 12/1967 | Rottmann | 209/111.7 X |
| 3,515,475 | 6/1970 | Zukor | 356/163 |
| 3,684,385 | 8/1972 | Einfalt et al. | 356/240 |
| 3,836,261 | 9/1974 | Clarke | 356/163 X |

Primary Examiner—Alfred L. Brody
Attorney, Agent, or Firm—Gravely, Lieder & Woodruff

[57] ABSTRACT

Apparatus for and method of inspecting transparent containers of the type used for food and beverages for the presence of dirt, foreign objects and manufacturing defects, such as birdswings. The apparatus includes illuminating each container from different angles and in a sequential order, and processing the illuminated images by photo-electronic scanning apparatus to obtain a response on a change in the illumination level within an electronic window of an amount sufficient to actuate a container reject mechanism.

22 Claims, 5 Drawing Figures

CONTAINER INSPECTION APPARATUS AND METHOD OF INSPECTION

BACKGROUND OF THE INVENTION

The inspection of containers can be accomplished in several ways. One way is to look into the container from its filling opening or mouth and either rotate the container or not rotate it and rotate the scanning device. Another way is to illuminate the container from the side and rotate the container while in the view of the scanning device. Still other ways are to combine the first two inspection means by using some features and omitting other features. High speed container movement greatly restricts the character of means that can be used to obtain the desired inspection results, such as means wherein the containers must be rotated to obtain a scan of the interior. When rotation is not feasible then multiple stop inspection stations and individual scanning devices for each station are sometimes used.

An electronic inspection apparatus has been disclosed in Richards U.S. Pat. No. 2,798,605 where a plurality of television cameras are used to inspect bottles from a plurality of angles. In this disclosure each view of the bottle required an individual camera, or several observations could be made simultaneously since there were several cameras available for that purpose. The cameras in this patent are not capable of making observations from several different sides of the container, and as a result the apparatus is exceedingly expensive and requires more space along the conveyor than is normally available. The complexity of tuning a plurality of cameras is very great and the possibilities of the containers deviating from a desired path adds to the problem of obtaining sharp pictures and accurate inspection.

SUMMARY OF THE INVENTION

This invention relates to apparatus for inspecting transparent containers for dirt and foreign objects inside the container, and manufacturing flaws without requiring rotation of the container, and the invention also relates to a method of inspecting containers.

The apparatus, by which the method may be put into use, utilizes an arrangement of means furnishing a light source which illuminates the containers from two directions as the container is moved, without rotation, on a suitable conveyor. The light is processed after passing through the container by an arrangement of mirrors, lenses and a beam-splitting unit so that superimposed images of the different views of the container are seen by a single photo-electronic scanning apparatus which scan the images sequentially.

Important objects of the present invention are to illuminate the container from different angles to give a total surface illumination through spaced apart pulsed light beams, to minimize the effects of stray reflections from the exterior surfaces of the container by placement of the light source and scanning devices on opposite sides of the container, to project two images of the same container through an optical system which combines the light rays of each image in a path leading to the scanning means that observes the images individually at the same position, to use only one scanning means for inspecting the whole body of each container and electronically limiting the inspection area to the container contour so that non-uniformities around the container edges do not produce false signals, and to scan opposite surfaces of containers with a single sensing system while the containers are in motion.

Other objects of this invention will be pointed out in the following description of a presently preferred embodiment of container inspection apparatus having a conveyor for moving a line of transparent container spaced apart through an inspection zone in which illumination is directed upon two different sides of the container, and characterized in that the container is immersed in a uniformly diffused volume of light so that an optical system of mirrors, lenses and beam processing means develops two images of the container for successive examination by photo-electronic scanning apparatus.

The embodiment herein disclosed practices the method of inspecting a line of containers on the move through an inspection station which illuminates the container from two different sides so as to form two images, characterized in that each image is directed along a predetermined path by means capable of separating the images and sequentially measuring the changes in the illumination levels so that significant changes can be detected and the offending container removed from the moving line.

BRIEF DESCRIPTION OF THE DRAWINGS

A preferred embodiment of the present invention is disclosed in the accompanying drawings wherein.

DESCRIPTION OF THE EMBODIMENTS

Figure 1:
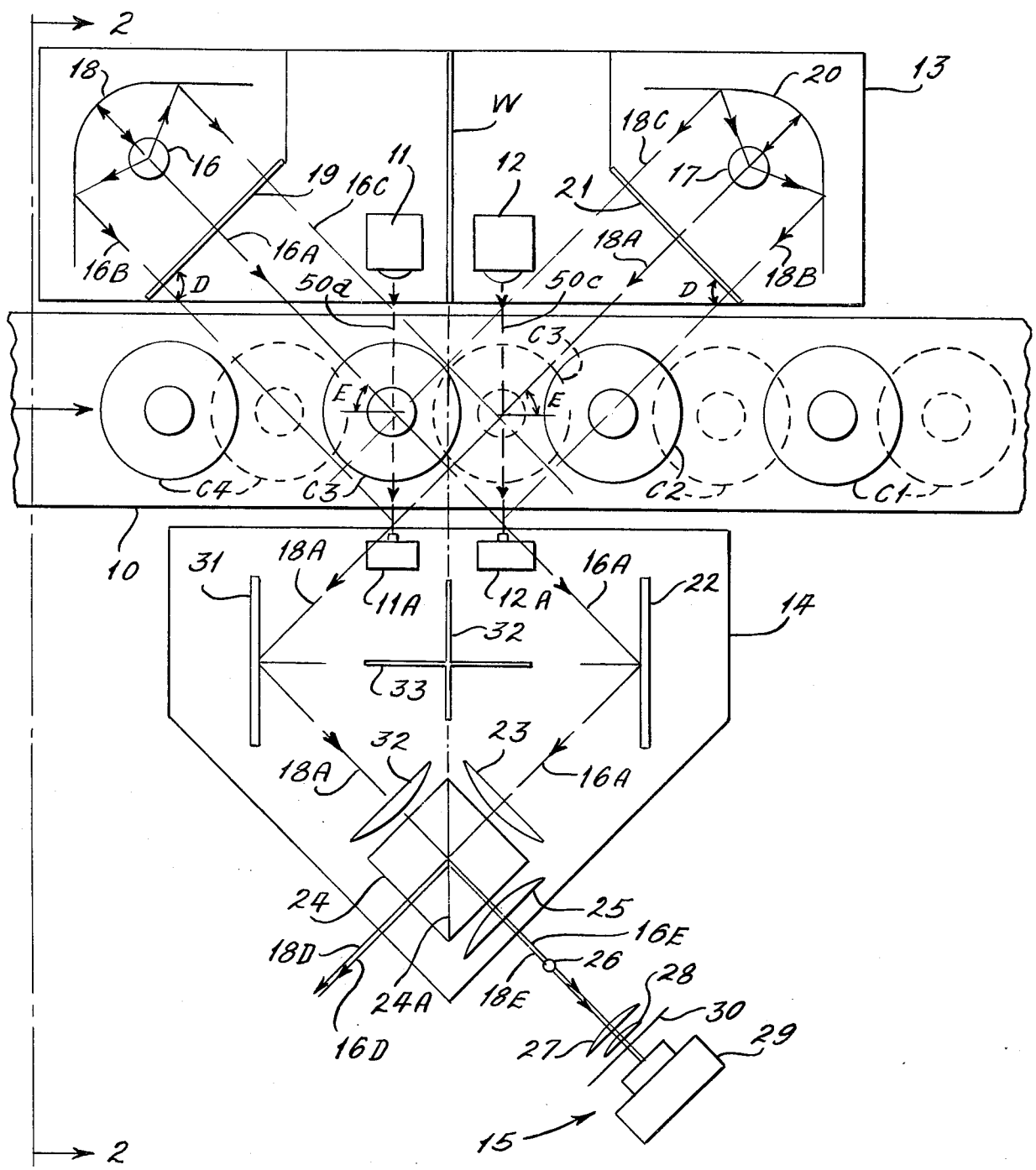
FIG. 1 is a schematic plan view of a conveyor moving containers in front of a source of illumination and a system of mirrors, lenses, beam-splitters and photo-electronic scanning means to perform the inspection function.
Figure 5:
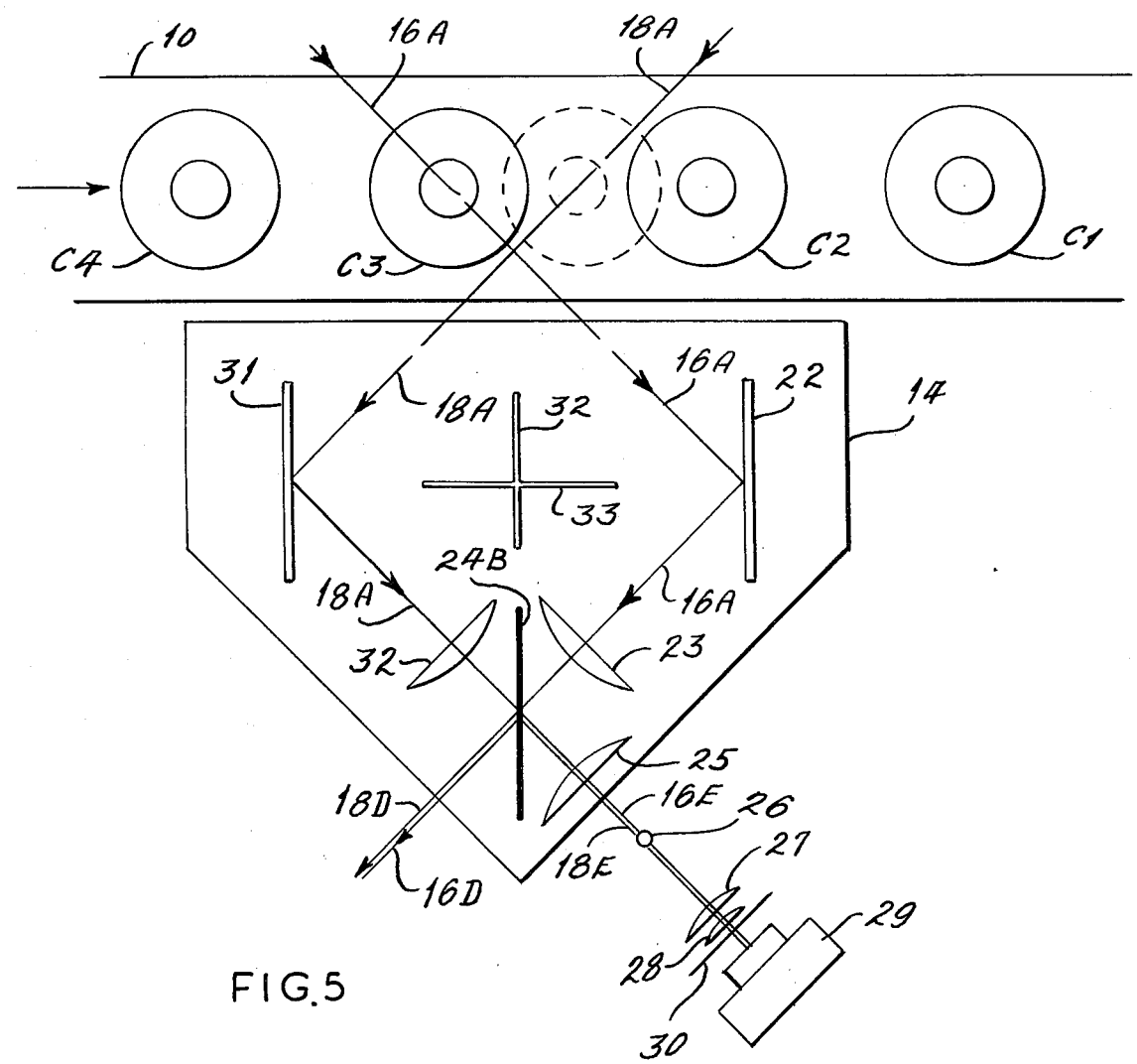
FIG. 5 is a schematic plan view of a modification in the apparatus for inspecting containers seen in FIG. 1.

In the drawings a preferred embodiment is seen in FIG. 1, and a modification has been disclosed in FIG. 5.

Figure 3:
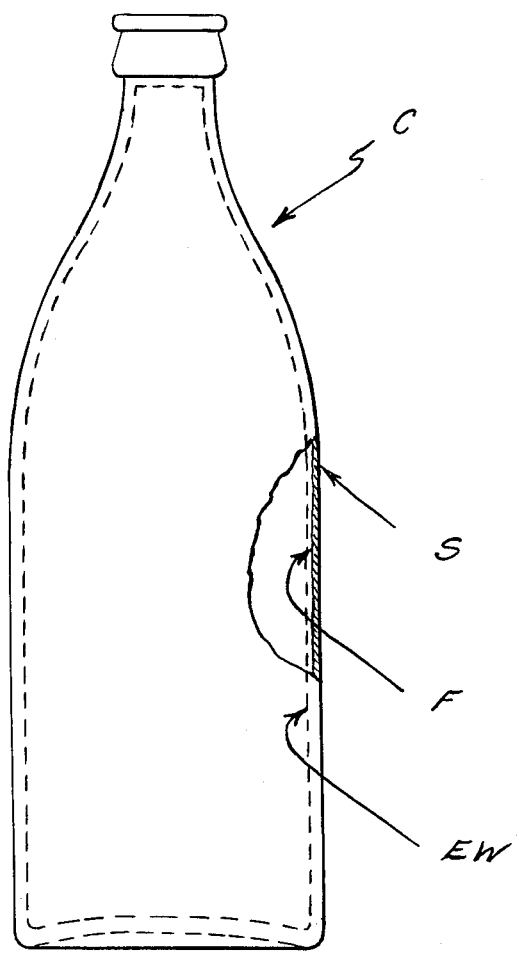
FIG. 3 is an elevational view of a transparent container with the side wall shadow shown between the outer contour of the container image and the field of view or window scanned by the photo-electronic means.

In view of FIG. 1, the schematic disclosure of apparatus is arranged to inspect each transparent container as it is moved through an inspection zone. The inspection is performed by photo-electronic means which is capable of looking at and responding to the area EW of the container C shown, for example, in FIG. 3. This area EW is to be known as the electronic window because it is an area which excludes the fringe shadows F which can vary in thickness depending on the variations from uniform thickness of the wall of the container. The outer limit of the fringe shadow F is the silhouette S or image of the container C. Foreign objects on the inside surface of the container will be within the electronic window EW and will change the transmission of light thrown on the container.

In FIG. 1 the containers C are moved in equally spaced relation on a conveyor 10 which is driven rightwardly so that the containers pass through the inspection zone which is located by the spaced light beam device 11 and 12. The first device 11 directs a light beam across the line of container travel to a photocell 11A or other equivalent sensing element. The second device 12 is spaced downstream from device 11 about the length of one-half the initial spacing length between containers, and it too directs a light beam across the line of travel of containers C to a sensing element 12A. The equal or uniform spacing is determined by the need to prevent a container in front of and also to the rear of a container undergoing inspection from blocking off any portion of light directed onto the container being inspected. In FIG. 1 the containers C1, C2, C3 and C4 are shown in full line, and container C3 has interrupted the light beam between the source 11 and the sensor 11A. An inspection of container C3 is performed and when that container C3 interrupts the light beam between the source 12 and the sensor 12A it will be in the position seen in broken line. Thus the spaced containers C are shown first in full line for the first inspection station in the zone and then in broken line for the second inspection station in the zone.

Figure 2:
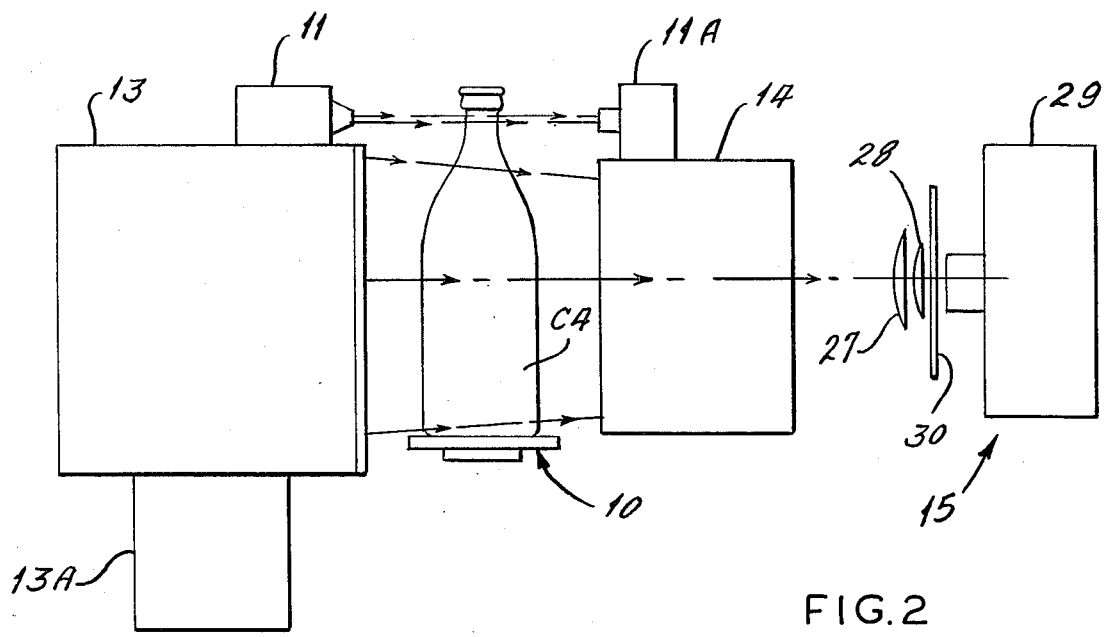
FIG. 2 is an elevational view, again in schematic arrangement, taken along line 2—2 in FIG. 1.

The apparatus in FIG. 1 includes a source of light assembled in a light box 13 located at one side of the path of conveyor 10, an optical system in a suitable housing 14 located at the opposite side of the conveyor from the light box 13, and beyond the housing 14 there is disposed photo-electronic scanning apparatus 15. The light box 13 is divided into compartments by a central wall W with linear flash tube 16 in one compartment and a similar flash tube 17 in the other. The flash tube 16 is located at the focus of a cylindrical parabolic reflector 18 and is connected to a high voltage power supply in the housing 13A (FIG. 2). The tube 16 is activated by a pulse which is produced each time a container interrupts the light beam between devices 11 and 11A. The pulsed light flash is of very short duration, being of the order of 0.5 millisecond or less. In a similar manner, the other flash tube 17 is connected to the same high voltage power supply in housing 13A and is pulsed when a container breaks the light beam between the devices 12 and 12A. The duration of this second light flash is short and of the same order as for the tube 16.

The pulsing of the flash tube 16 produces a beam of light which may be defined by a central filament 16A and respective marginal filaments 16B and 16C which are derived from the polished surface of the reflector 18. The total light beam passes through a diffuser plate 19 made of glass or plastic, and this plate is set at an angle D of 40° to 50° to the line of container travel so that the container in the light beam station location corresponding to devices 11 and 11A will be uniformly illuminated to down grade the effects of waves and smiles on the container walls. The container, and in this case container C3, will be fully immersed in the illumination from reflector 18 and travelling in the general direction of light filament 16A. The pulsing of flash tube 17, likewise produces a beam of light which may be defined by a central filament 18A, and respective marginal filaments 18B and 18C, alll derived from the polished surface of the reflector 20. The illumination passed through a diffuser plate 21, like the plate 19, which is set at an angle D of 40° to 50° to the line of conveyor travel. The pulsing of the flash tube 17, occurs only when the container C3 reaches the station where it interrupts the light beam between devices 12 and 12A (the broken line position in FIG. 1). Thus, in the first station of the inspection zone the flash tube 16 is energized in response to the interruption of the light beam between devices 11 and 11A, and the flash tube 17 is energized in response to the interruption of the light beam between devices 12 and 12A. In each instance the flash tubes 16 and 17 obtain the energy from the high voltage power supply in housing 13A, and the pulsed light flash is of very short duration, being of the order of 0.5 millisecond or less.

In FIG. 1 a plurality of containers C1, C2, C3 and C4 are shown in equal and uniformly spaced relation in full line. Container C3 is in the first station of the inspection zone and is immersed in the light from flash tube 16. It is noted that the trailing container C4 does not block any part of the light as it is out of the margin of the light as represented by the filament 16B. When the container C3 moves to the broken line position it attains the second station in the inspection zone and is illuminated by the light from flash tube 17. When the second flash occurs with container C3 in the broken line position, the leading container C2 has also moved to the broken line position where it does not block the light as represented by the filament 18B. The spacing of the containers, therefore, meets the requirement that leading and trailing containers must not block or cut into the total light generated by the flash tubes 16 and 17 at each successive short duration flash.

The side of the conveyor 10 (FIGS. 1 and 2) opposite the light box is occupied by a suitable housing 14 for the optical system. The housing has an open side facing the conveyor so that the successive light flashes may be received. In the following description it will be understood that reference to the path taken by each light filament 16A and 18A will mean the general path of the total light beams from the respective flash tubes.

First, dealing with the light from flash tube 16, it can be seen that the filament 16A impinges on the first surface of a mirror 22, whose first surface plane is set at right angles to the line of conveyor travel which places it at 45° to the incident light filament 16A. It is desirable to use first surface mirrors to obtain maximum illumination efficency and least irregularity of light path. The reflected light filament will pass through the lens 23 with focal point on the longitudinal axis of the containers of the first station. The lens 23 will collimate the light entering a beam-splitting prism 24, mounted to accept the light filament 16A from the lens 23. The prism has a reflective surface 24A which is at 45° to the accepted light 16A. The prism surface 24A is selected to have equal transmittance and reflectance so that there will be a transmitted portion 16D of the filament 16A and a reflected portion 16E, each of which emerges from the prism and strikes lens 25 which collects the light at its focal point 26. The focal plane of lens 25 will have a real image of the container C3 at the point 26.

Having established a real image of the container C3 at the point 26, it is projected by suitably chosen lenses 27 and 28 onto a photo-electronic or television scanning unit 29, having a necessary filter 30 of a predetermined optical characteristic. The filter 30 is selected from a group which are used selectively to compensate for color variations in the containers and to attenuate the ambient light reflections. The partition W in the light box 13 is provided to optically isolate the two flash tubes 16 and 17 so that stray light reflections will not enter the optical system in housing 14 and produce ghosts in the scanning unit 29.

When the container C3 moves into the second station in the inspection zone it triggers flash tube 17 to obtain a beam of light at right angles to the first described beam. The second beam of light is easily followed by noting the path of the filament 18A which enters the housing 14 and strikes the first surface of mirror 31 at 45° so that the reflected path of the filament 18A is at right angles to the reflected path of the first light filament 16A. The filament 18A enters lens 32 and passes into the beam-splitting prism surface 24A. The transmitted light filament 18E is collected by lens 25 at its focal point 26 where an image of the container C3 is made. As before described, the lenses 27 and 28 project the container image through the filter 30 onto the photo-electronic scanning unit 29.

It appears from the foregoing that the optical system in housing 14 receives light through the inspection zone. By the use of first surface mirrors and a beam-splitting prism the system will produce a reflected portion and a transmitted portion for each light beam coming from different sides of the container. The optical system recombines the reflected portion of the light represented by filament 16E with the transmitted portion of the light represented by filaments 18E, and since the prism has equal transmittance and reflectance characteristics the combined light filaments will have equal intensities when producing the container images at the focal plane of lens 25. It is to be remembered that the container images are not produced simultaneously, but are produced sequentially and are not therefore superimposed. Thus, sequential viewing of the same container at two different stations by the same scanning unit will fulfill the inspection of the whole container. The housing 14 is provided with internal baffles 32 and 33 to intercept stray light and prevent ghosts and impairment of the fidelity of the illuminated container images.

While it has not been shown in the drawings, and particularly FIG. 2 thereof, it is understood that conventional means may be employed to move the box 13 and housing 14 vertically so that the light source and optical system may be aligned with the position of the containers supported on and moved by the conveyor 10. Also, due to the positional tolerances of the mirrors 22 and 31 and the beam-splitter prism 24 parallax will be produced between two images at the focal plane 26 of the lens 25. Therefore, adjustment means (not shown) for the prism 24 is used to vary the angular position to compensate for parallax.

A modification of the apparatus described in connection with FIG. 1 is shown in FIG. 5, and wherever possible the same reference characters will be used to denote the parts and components previously described. The essential difference is that the beam-splitter prism 24 of FIG. 1 is eliminated in FIG. 5 and a beam-splitting mirror 24B is substituted. The mirror 24B has equal transmittance and reflectance characteristics so that the container images at the focal plane 26 will have the same intensities.

Figure 4:
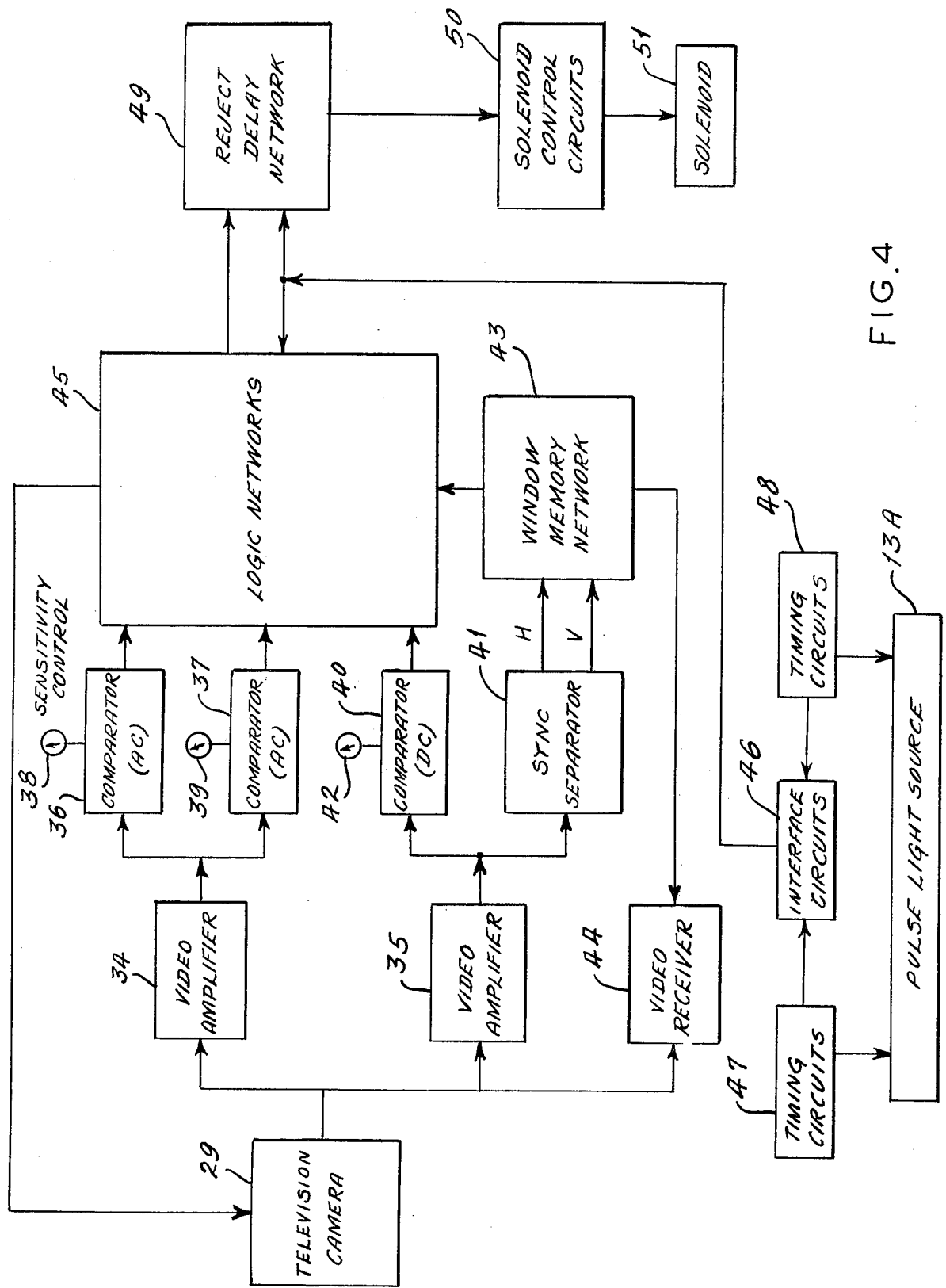
FIG. 4 is an electrical block diagram of the inspection apparatus seen in FIG. 1.

Turning now to FIG. 4 it can be seen that the photo-electronic scanning unit 29 produces signals due to the individual images of each container. The signals are fed to two video amplifiers 34 and 35. Amplifier 34 feeds two comparator networks 36 and 37 which detect the AC change in the image area. When an unwanted object exists within the container image the comparators 36 and 37 will detect the changes in the illumination level at the point where the object is located against the uniform character of the background illumination. Comparator 36 will detect the light-to-dark change, while the comparator 37 will detect the dark-to-light change, due to the edges of the object within the image area. Sensitivity control means 38 and 39 for the respective comparators 36 and 37 determine the threshold setting for comparing signals due to the unwanted object against the reference level.

Amplifier 35 feeds the video signals to the DC comparator 40 and to the synchronising pulse separator 41. The DC comparator 40 is used to detect the gross change in illumination level and compares this change with an adjustable reference level determined by the sensitivity control 42. The synchronising pulse separator networks 41 separates the horizontal (H) and vertical (V) synchronising pulses from the video signals, and these pulse trains feed the window memory network 43 which produces an electronic window (EW) within the image of the container as described in reference to FIG. 3. As noted before, the electronic window EW is shaped and sized so that non-uniformity of the fringe F can be eliminated. This is monitered by a video receiver network 44 which receives the video signals from the photo-electronic unit 29 (a television camera) and from the window memory network 43. The result is that the display of the electronic window can be adjusted to be accurately superimposed on the container image or silhouette S of FIG. 3.

The signals from the comparators 36, 37 and 40, and signals from window memory network 43 are fed to the logic circuits in network 45 which is the central processing network. This central processing network 45 is triggered by a timing pulse generated at the interface circuit 46, and the latter circuit 46 is alternately responsive to the light beam sensors 11A and 12A which detect the arrival of containers at the respective stations in the inspection zone. The light sources 11 and 12 are mounted (FIG. 2) on the box 13 and each emits a continuous and narrow column or beam of light onto the photo-sensitive sensors 11A and 12A respectively. The beam of light from source 11 is interrupted by the container which then moves to the second station and interrupts the beam from light source 12. The first interruption triggers a timing circuit 47 which produces a pulse of light from flash tube 16 and simultaneously feeds a signal to the interface circuit 46 which, in turn, produces a pulse to trigger the logic network 45. The second interruption at light source 12 triggers a pulse of light from flash tube 17 and this is accompanied by activity in a timing circuit 48 and the interface circuit 46. The latter circuit produces a pulse to trigger the logic network 45. Each time the logic network 45 is triggered it processes the container image within the electronic window area and if there is a foreign object detected the resulting pulse is fed to a reject delay network 49. The reject signal from the network 45 is delayed by network 49 so that when the faulty container arrives at a predetermined position the solenoid control circuit 50 will be energized at the expiration of the time delay to operate a solenoid 51 which effects removal of the offending container from the conveyor 10 at the predetermined place downstream from the inspection zone.

In operation, the containers on the conveyor 10 travel at such velocity that an unblurred image is not possible unless the flash of light is bright and of very short duration. The photo-electronic sensors 11A and 12A are used to ensure that the containers are illuminated when in proper position with respect to the light source and photo-electronic scanner. The apparatus described herein provides a sharp image of the rapidly moving container. The photo-electronic unit 29 transforms the image of volume of the container into electrical signals by means of the electron beam which scans the sensitive screen. For three inch diameter containers moving at the rate of 800 containers per minute, a single container would move approximately 0.7 inches during the scanning time of the unit 29. This extent of movement requires that the illumination of the container must be very short to obtain a sharp image, such as less than 0.5 millisecond, and on the order of 0.1 millisecond. As before described, if there is a change in the light level within the electronic window EW that container is removed from the conveyor, and if there is no change in the light level the logic networks 45 makes no response.

The foregoing description has set forth two forms of the apparatus by which this invention may be put into practice, but is understood that other arrangements may come to mind based on the principles herein disclosed.

We claim:

1. In container inspection apparatus, the improvement which comprises: means to move light transparent containers along a predetermined path having spaced apart container inspection stations, said moving means positioning each container in a predetermined position free of rotation during inspection, a source of illumination for each inspection station to project a light beam along a path through an inspection station, the light beam for one inspection station illuminating a side of the container thereat from an angle different from the angle of the beam of light for illuminating a different side of the container in another inspection station, such that each container is illuminated from two different sides, sensing means at each inspection station to sense the arrival of a container and activate the source of illumination for that station, said inspection stations being separated a distance such that when one sensing means activates its source of illumination the other sensing means is inactive, photo-electronic scanning means to scan container images illuminated by said sources of illumination, mirror means positioned in the light beam paths beyond the containers from said source of illumination, said mirror means being set to direct the light beam passing through each container toward a common point, light beam directing means at said common point to arrange the light beams for travel along a common path directed at said photo-electronic scanning means, and means responsive to said scanning means to compare the level of illumination in each light beam with a predetermined standard level of illumination.

2. The inspection apparatus of claim 1 wherein said source of illumination is a linear flash tube with an axis of elongation substantially parallel with the container axis, and the activation thereof is of short duration of the order of less than 0.5 millisecond.

3. The inspection apparatus of claim 1 wherein said source of illumination is activated sequentially and only as containers are sensed sequentially at the inspection stations.

4. The inspection apparatus of claim 1 wherein each source of illumination includes a linear flash tube, a reflector and diffuser to immerse the whole container in a diffused volume of light.

5. The inspection apparatus of claim 1, wherein said source of illumination consists of a separate linear flash tube adjacent each inspection station, said mirror means directs the illumination into paths crossing at right angles to each other at said common point, beam-splitting means in the crossing paths of illumination to direct the illuminated images in said common path, and lens means to collect the illuminated images in said common path at its focal plane.

6. The inspection apparatus of claim 1 wherein said scanning means sees the whole container image when illuminated at each inspection station, and said comparing means includes electronic networks creating an electronic window less than the size of the whole container image to exclude the fringe portion of the container image.

7. In container inspection apparatus for inspecting transparent containers the improvement which comprises: means to move the transparent containers through inspection stations spaced apart so that the containers pass through the stations sequentially, said moving means presenting the containers in said inspection stations free of rotation, a separate source of illumination adjacent each inspection station, each illumination source being effective to illuminate the whole container at one time but from different sides thereof, means at each inspection station to sense the arrival of a container and activate said source of illumination for said station, mirror means spaced from each of said inspection stations opposite said source of illumination and arranged to receive the illuminated images of the containers at said inspection stations and reflect the images along paths which have a common point where the images sequentially cross, image scanning means directed to look at said common point for inspecting the container images illuminated from the different sides, and optical means at said common point to direct the reflected images into said image scanning means.

8. The inspection apparatus of claim 7 wherein said optical means directs the separately illuminated images of the container into said image scanning means sequentially in the order of energization of said illumination means.

9. The inspection apparatus of claim 7 wherein said sources of illumination are elongated tubes which emit a flash of light of less than 0.5 millisecond duration, and each of said tubes provides a linear flash of light to immerse the entire container in illumination.

10. The inspection apparatus of claim 7 wherein said angular displacement of the illuminated sides of the container illumination means is located in spaced relation for illuminating the sides of the containers which are displaced by approximately 90°.

11. The inspection apparatus of claim 7 wherein said optical means includes beam-splitting means, lens means cooperating with said beam-splitting means to locate real images of the container in the focal plane of said lens, and said image scanning means is focused at said focal plane.

12. The inspection apparatus of claim 7 wherein said image scanning means includes a photo-electronic unit receiving the illuminated image of the container and circuit networks connected to said unit to restrict the scanning to an electronic window area of the container image.

13. Container inspection apparatus comprising means moving light transparent containers along a predetermined path, a pair of sources of illumination adjacent one side of said container moving means to direct the illumination across said moving means and along different paths, each path crossing said moving means defining an inspection station, means responsive to the movement of containers through said inspection stations to energize each of said sources of illumination in sequence and produce an entire container image, electronic scanning means positioned at the opposite side of said container moving means and spaced from said inspection stations, and means in the space between said scanning means and said inspection stations to collect the illuminated container image from each successive flash and direct the same into the scanning means, whereby each container is illuminated by each of said pair of illumination sources and is correspondingly scanned.

14. The container inspection apparatus of claim 13 wherein said different paths for said illumination are at approximately 90° to each other, and said collecting means redirects the illumination into a common path.

15. The container inspection apparatus of claim 13 wherein said collecting means consists of mirrors and beam-splitting means, and said scanning means is a photo-electronic device.

16. The container inspection apparatus of claim 13 wherein said short duration of said brilliant light flashes is in each instance of the order of less than 0.5 millisecond.

17. The container inspection apparatus of claim 13 wherein said scanning means comprises electronic control means adjustable to limit the field of scan to less than the entire container image.

18. The container inspection apparatus of claim 17 wherein said control means adjusts the limits of the field of scan in directions perpendicular to each other.

19. A method of inspecting transparent containers for foreign objects consisting in moving containers through two inspection zones, illuminating each container sequentially and from different sides in said inspection zones to produce two different illuminated images, transmitting the two illuminated images into a common path sequentially, and scanning the two images sequentially to detect changes in the level of illumination relative to a predetermined desired level of illumination.

20. The method set forth in claim 19 and including moving the containers through the inspection zone at a speed of the order of approximately 800 containers per minute, and illuminating the containers in the time span of the order of less than 0.5 millisecond to obtain a substantially motion free image.

21. The method set forth in claim 19 and including directing the two illuminated images of each container to cross at a predetermined location, and collecting the crossing images in said common path.

22. The method set forth in claim 19, and including the illumination of each container sequentially from said different sides, directing one of the illuminated images along a predetermined first path and directing the other one of said illuminated images along a second path which intersects said first path, and redirecting one of said images such that both images are caused to travel along one of said paths in sequence of illumination.

* * * * *